United States Patent
Cully et al.

(10) Patent No.: US 11,679,240 B2
(45) Date of Patent: *Jun. 20, 2023

(54) REMOVABLE COVERS FOR DRUG ELUTING MEDICAL DEVICES

(71) Applicant: W. L. Gore & Associates, Inc., Newark, DE (US)

(72) Inventors: Edward H. Cully, Flagstaff, AZ (US);
Jeffrey B. Duncan, Flagstaff, AZ (US);
Peter Heicksen, Flagstaff, AZ (US);
Joseph B. Koenig, Flagstaff, AZ (US);
Jeffrey J. Kustusch, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 609 days.

This patent is subject to a terminal disclaimer.

(21) Appl. No.: 16/783,612

(22) Filed: Feb. 6, 2020

(65) Prior Publication Data
US 2020/0188645 A1    Jun. 18, 2020

Related U.S. Application Data

(63) Continuation of application No. 14/872,439, filed on Oct. 1, 2015, now Pat. No. 10,569,063.
(Continued)

(51) Int. Cl.
*A61M 25/10*    (2013.01)
*A61F 2/97*    (2013.01)
(Continued)

(52) U.S. Cl.
CPC ......... *A61M 25/10184* (2013.11); *A61F 2/95* (2013.01); *A61F 2/958* (2013.01);
(Continued)

(58) Field of Classification Search
CPC ........ A61M 25/10184; A61M 25/0668; A61M 2025/0681; A61M 2025/105; A61M 2025/1081; A61F 2/97; A61F 2/958
See application file for complete search history.

(56) References Cited

U.S. PATENT DOCUMENTS 4,306,562 A    12/1981    Osborne
4,798,876 A    1/1989    Gould et al.
(Continued)

FOREIGN PATENT DOCUMENTS

EP    2661244 B1    10/2015
WO    01/08599 A1    2/2001
(Continued)

OTHER PUBLICATIONS

International Preliminary Report on Patentability received for PCT Patent Application No. PCT/US2015/053770, dated Apr. 13, 2017, 8 pages.
(Continued)

*Primary Examiner* — Nathan R Price
*Assistant Examiner* — Melissa A Snyder

(57) ABSTRACT

The present disclosure includes an expandable medical device and outer sheath combination. The outer sheath is capable of being split to form multiple sheath sections that may be peeled back to expose a portion or all of the expandable medical device. The medical device, as well as the outer sheath, may include one or more therapeutic agents for delivery to a treatment area within a patient.

19 Claims, 8 Drawing Sheets

Related U.S. Application Data

(60) Provisional application No. 62/075,574, filed on Nov. 5, 2014, provisional application No. 62/059,408, filed on Oct. 3, 2014.

(51) Int. Cl.
*A61L 29/04* (2006.01)
*A61L 29/08* (2006.01)
*A61M 25/06* (2006.01)
*A61F 2/958* (2013.01)
*A61F 2/95* (2013.01)

(52) U.S. Cl.
CPC .............. *A61F 2/97* (2013.01); *A61L 29/041* (2013.01); *A61L 29/085* (2013.01); *A61M 25/0668* (2013.01); *A61F 2002/9583* (2013.01); *A61M 25/1011* (2013.01); *A61M 2025/0681* (2013.01); *A61M 2025/105* (2013.01); *A61M 2025/1081* (2013.01)

(56) References Cited

U.S. PATENT DOCUMENTS

| | | | |
|---|---|---|---|
| 5,195,978 | A | 3/1993 | Schiffer |
| 5,246,452 | A | 9/1993 | Sinnott |
| 5,304,121 | A | 4/1994 | Sahatjian |
| 5,647,857 | A | 7/1997 | Anderson et al. |
| 5,662,703 | A | 9/1997 | Yurek et al. |
| 5,755,769 | A | 5/1998 | Richard et al. |
| 5,765,682 | A | 6/1998 | Bley et al. |
| 5,964,730 | A | 10/1999 | Williams et al. |
| 6,019,787 | A | 2/2000 | Richard et al. |
| 6,039,755 | A | 3/2000 | Edwin et al. |
| 6,254,628 | B1 | 7/2001 | Wallace et al. |
| 6,447,540 | B1 | 9/2002 | Fontaine et al. |
| 6,669,719 | B2 | 12/2003 | Wallace et al. |
| 6,899,727 | B2 | 5/2005 | Armstrong et al. |
| 6,939,327 | B2 | 9/2005 | Hall et al. |
| 8,070,824 | B2 | 12/2011 | Burnett et al. |
| 8,202,309 | B2 | 6/2012 | Styrc |
| 8,308,789 | B2 | 11/2012 | Armstrong |
| 8,414,528 | B2 | 4/2013 | Liu et al. |
| 8,414,909 | B2 | 4/2013 | Wang |
| 8,545,544 | B2 | 10/2013 | Spenser et al. |
| 2001/0001128 | A1 | 5/2001 | Holman et al. |
| 2001/0003161 | A1 | 6/2001 | Vardi et al. |
| 2003/0004561 | A1 | 1/2003 | Bigus et al. |
| 2004/0143272 | A1 | 7/2004 | Cully et al. |
| 2006/0015171 | A1 | 1/2006 | Armstrong |
| 2006/0151171 | A1 | 7/2006 | Davies et al. |
| 2007/0198077 | A1* | 8/2007 | Cully .................. A61F 2/97 623/1.13 |
| 2008/0118544 | A1 | 5/2008 | Wang |
| 2008/0140003 | A1 | 6/2008 | Bei et al. |
| 2008/0255580 | A1 | 10/2008 | Hoffman et al. |
| 2009/0112239 | A1 | 4/2009 | To |
| 2009/0182278 | A1 | 7/2009 | Eversull et al. |
| 2010/0228333 | A1 | 9/2010 | Drasler et al. |
| 2010/0249907 | A1 | 9/2010 | Dorn et al. |
| 2011/0060397 | A1 | 3/2011 | Dorn |
| 2012/0310210 | A1 | 12/2012 | Campbell et al. |
| 2013/0018309 | A1 | 1/2013 | Ewing et al. |
| 2013/0226279 | A1 | 8/2013 | Slattery et al. |
| 2013/0253426 | A1 | 9/2013 | Campbell et al. |
| 2014/0066897 | A1 | 3/2014 | Campbell et al. |
| 2015/0005809 | A1 | 1/2015 | Ayres et al. |
| 2016/0096006 | A1 | 4/2016 | Cully et al. |

FOREIGN PATENT DOCUMENTS

| | | |
|---|---|---|
| WO | 2004/066809 A2 | 8/2004 |
| WO | 2006/019626 A2 | 2/2006 |
| WO | 2009/012163 A1 | 1/2009 |

OTHER PUBLICATIONS

International Search Report and Written Opinion issued in PCT/US2015/053770, dated Dec. 14, 2015, 11 pages.

\* cited by examiner

REMOVABLE COVERS FOR DRUG ELUTING MEDICAL DEVICES

CROSS-REFERENCE TO RELATED APPLICATION

This application is a continuation of U.S. patent application Ser. No. 14/872,439, filed Oct. 1, 2015, now U.S. Pat. No. 10,569,063, granted Feb. 25, 2020, which claims the benefit of U.S. Provisional Application 62/075,574, filed Nov. 5, 2014, and also claims the benefit of U.S. Provisional Application 62/059,408, filed Oct. 3, 2014, all of which are incorporated herein by reference in their entireties for all purposes.

FIELD

The present disclosure generally relates to endoprostheses for treating diseases of the vasculature and similar anatomies, and more particularly, to therapeutic agent delivery systems which employ splittable and removable delivery sheaths.

BACKGROUND

The systemic administration of therapeutic agents treats the body as a whole even though the disease to be treated may be localized. In some cases of localized disease, systemic administration may not be desirable because the drug agents may have unwanted effects on parts of the body which are not to be treated or because treatment of the diseased part of the body requires a high concentration of a drug agent that may not be achievable by systemic administration.

It is therefore often desirable to administer therapeutic agents to only localized sites within the body. Common examples of where this is needed include cases of localized disease (e.g., coronary heart disease) and occlusions, lesions, or other disease in body lumens. Several devices and methods for localized drug delivery are known. In one example, such devices are drug delivery balloons, and methods of their use include the steps of coating a balloon attached to a balloon catheter with a drug and optionally a carrier matrix, inserting the catheter into a blood vessel, tracking the balloon to a desired location, and expanding the balloon against the surrounding tissue to transfer the drug locally at the intended treatment area.

One of the potential drawbacks to localized drug delivery is the possibility of premature or unintended release of the drug, the carrier matrix, and/or the drug/carrier matrix combination. This may occur during tracking and placement at the treatment area of a drug delivery device and post delivery as the device is withdrawn from the body. Such unintended release may result from drug diffusion, device contact with areas proximate the treatment area, or washing of the drug from the surface of the delivery device due to blood flow. This is of particular concern when the device comprises a therapeutic agent of a type or dosage not intended to be released to tissue or blood outside the treatment area. Further, drug may be prematurely released from the outer surface of the delivery device by friction generated by sliding a retractable cover over the balloon surface.

In view of the potential drawbacks to current, localized drug delivery, there exists a need for devices and methods that allow for controlled, localized delivery of drug agents, especially soluble agents, to specific treatment areas within a mammalian body that avoids particulation and premature or unintended drug release away from the intended treatment area, while ensuring that desired dosing occurs.

SUMMARY

Various disclosed concepts relate to a medical device. According to one example ("Example 1"), a medical device includes an expandable medical device; and a tubular sheath surrounding at least a portion of the expandable medical device, wherein the tubular sheath is configured to split upon a proximally directed application of tension being applied to a distal end of the tubular sheath, and wherein the tubular sheath is configured such that a split portion of the tubular sheath is adapted to be everted inwardly and removed from surrounding the expandable medical device by extending between the tubular sheath and the expandable medical device.

According to another example further to Example 1 ("Example 2"), the medical device further comprises an activation line coupled to the distal end of the tubular sheath, the activation line extending between the tubular sheath and the expandable medical device.

According to another example further to Example 2 ("Example 3"), the sheath is configured to split into a first sheath segment and a second sheath segment, and wherein the activation line includes a first portion attached to the first sheath segment and a second portion attached to the second sheath segment, the first and second sheath segments being adapted to be everted inwardly and removed from surrounding the expandable medical device by extending between the tubular sheath and the expandable medical device.

According to another example further to either Example 2 or 3 ("Example 4"), the tubular sheath has an inner surface and the expandable medical device has an outer surface, and wherein the split portion of the tubular sheath is adapted to be everted inwardly and removed from surrounding the expandable medical device by extending between the inner surface of the tubular sheath and the outer surface of the expandable medical device.

According to another example further to either Example 3 or 4 ("Example 5"), the first sheath segment is removable from surrounding the expandable medical device prior to the second sheath segment being removed from surrounding the expandable medical device.

According to another example further to any of Examples 3 to 5 ("Example 6"), a length of the first portion of the activation line is shorter than a length of the second portion of the activation line.

According to another example further to any of Examples 2 to 6 ("Example 7"), the expandable medical device is a first balloon, the medical device further comprising a second balloon having a higher compliance than a compliance of the first balloon, the second balloon being in fluid communication with the first balloon, wherein upon inflation of the second balloon, tension is applied to the activation line.

Various disclosed concepts relate to a medical device. According to one example ("Example 8"), the medical device includes an expandable medical device; and a tubular sheath surrounding at least a portion of the expandable medical device, the tubular sheath comprising a first sheath layer and a second sheath layer, wherein the tubular sheath is configured to split upon a proximally directed application of tension being applied to a distal end of the tubular sheath, and wherein the tubular sheath is configured such that a split portion of the tubular sheath is adapted to be everted inwardly and removed from surrounding the expandable medical device by extending between the first and second sheath layers.

According to another example further to Example 8 ("Example 9"), the medical device further comprises an activation line coupled to the distal end of the tubular sheath, the activation line extending between the first and second sheath layers.

According to another example further to Example 9 ("Example 10"), the the sheath is configured to split into a first sheath segment and a second sheath segment, and wherein the activation line includes a first portion attached to the first sheath segment and a second portion attached to the second sheath segment, the first and second sheath segments being adapted to be everted inwardly and removed from surrounding the expandable medical device by extending between the first and second sheath layers.

According to another example further to Example 10 ("Example 11"), the first sheath segment is removable from surrounding the expandable medical device prior to the second sheath segment being removed from surrounding the expandable medical device.

According to another example further to either Example 10 or 11 ("Example 12"), a length of the first portion of the activation line is shorter than a length of the second portion of the activation line.

According to another example further to any one of Examples 1 to 6 and 8 to 12 ("Example 13"), the expandable medical device is one of a balloon and a stent.

According to another example further to any one of Examples 9 to 12 ("Example 14"), the expandable medical device is a first balloon, the medical device further comprising a second balloon having a higher compliance than a compliance of the first balloon, the second balloon being in fluid communication with the first balloon, wherein upon inflation of the second balloon, tension is applied to the activation line.

According to another example further to any one of the preceding Examples ("Example 15"), the tubular sheath comprises an extruded polymeric tube.

According to another example further to any one of the preceding Examples ("Example 16"), the tubular sheath comprises a wrapped polymeric material.

According to another example further to any one of the preceding Examples ("Example 17"), the tubular sheath comprises a distensible and highly oriented polymeric material.

According to another example further to any one of the preceding Examples ("Example 18"), the tubular sheath comprises ePTFE.

According to another example further to any one of the preceding Examples ("Example 19"), a proximal end of the tubular sheath is secured to an elongate member.

BRIEF DESCRIPTION OF THE DRAWINGS

The features and advantages of the present disclosure will become more apparent from the detailed description set forth below when taken in conjunction with the drawings, wherein.

DETAILED DESCRIPTION OF THE ILLUSTRATED EMBODIMENTS

Figure 1A:
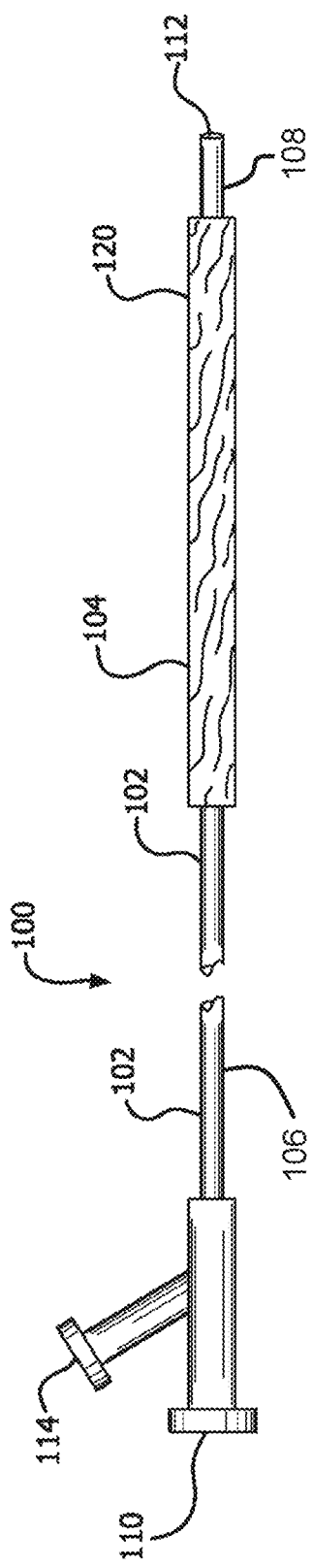
FIGS. 1A and 1B illustrate a side view and a cross sectional view of a medical device delivery system in accordance with the present disclosure.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

The terms "endoprosthetic device," "endoprosthesis," "vascular device," and the like can refer, throughout the specification and in the claims, to any medical device capable of being implanted and/or deployed within a body lumen. In various embodiments, an endoprosthesis can comprise a stent, a stent-graft, graft, a filter, an occluder, a balloon, a lead, and energy transmission device, a deployable patch, an indwelling catheter, and the like.

In addition, throughout this specification and claims, the delivery systems described herein can, in general, include an endoprosthesis constrained by a "covering member" or "sheath." The covering member or sheath can, in various embodiments, comprise a sheet of material that is fitted about an endoprosthesis. As used throughout the specification and in the claims, the term "elongate member" can refer to a shaft-like structure such as a catheter, guidewire, introducer sheath, or the like. In various embodiments, an endoprosthesis can be mounted or loaded on a catheter, also referred to herein as an inner shaft, and, in a constrained diameter, fit within an introducer sheath, also referred to herein as an outer shaft.

Further, the term "distal" refers to a relative location that is farther from a location in the body at which the medical device was introduced. Similarly, the term "distally" refers to a direction away from a location in the body at which the medical device was introduced.

The term "proximal" refers to a relative location that is closer to the location in the body at which the medical device was introduced. Similarly, the term "proximally" refers to a direction towards a location in the body at which the medical device was introduced.

With continuing regard to the terms proximal and distal, this disclosure should not be narrowly construed with respect to these terms. Rather, the devices and methods described herein may be altered and/or adjusted relative to the anatomy of a patient.

As used herein, the term "constrain" may mean (i) to limit expansion, occurring either through self-expansion or expansion assisted by a device, of the diameter of an expandable implant, or (ii) to cover or surround, but not otherwise restrain, an expandable implant (e.g., for storage or biocompatibility reasons and/or to provide protection to the expandable implant and/or the vasculature).

As used herein, the term "vessel" refers to any luminal or tubular structure within the body to which these constructs can be utilized. This includes, but not limited to, vascular blood vessels, vascular defects such as arteriovenous malformations, aneurysm, or others, vessels of the lymphatic system, esophagus, intestinal anatomy, sinuous cavity, uterus, or other. The embodiments of the present invention are also suitable for the treatment of a malignant disease (i.e. cancer) within or associated with a vessel With reference to FIG. 1A, a medical device delivery system 100 can comprise, for example, a medical device 104 mounted on an elongate member 102. The elongate member 102 can comprise, for example, a proximal end 106 and a distal end 108. In various embodiments, medical device delivery system 100 comprises a proximal guidewire lumen 110 that extends through the length of elongated member 102 and exits distal end 108 at a guidewire port 112. Such a catheter and balloon arrangement is typically referred to as an "Over The Wire" configuration. In other embodiments, elongate member 102 comprises guidewire port 112 located midway between proximal end 106 and distal end 108, which is typically referred to as a "Rapid Exchange" configuration.

Medical device delivery system 100 can also comprise, for example, a proximal inflation port 114 that allows fluid communication between elongate member 102 and a lumen of medical device 104, e.g. balloon 104. The length and inner and outer diameter of elongate member 102 are selected based upon the desired application of the medical device. For example, elongate member 102 generally has a circular cross-sectional configuration. However, oval and other cross-sectional configurations can also be used. For example, medical device delivery system 100 can be compatible with guidewires having diameters of 0.038", 0.035", 0.018" or 0.014", 0.010".

In various embodiments, medical device 104 comprises a balloon, such as, for example, a drug eluting balloon. Balloons useful in the invention can be blow-molded, can be non-compliant, compliant or semi-compliant, can be of various shapes, and may be "conformable" or "conforming" or "steerable" balloons. Balloon 104 can comprise, for example, balloons which are constructed of wrapped films, are fiber-wound, are of variable length, are segmented, and/or have controlled inflation profiles.

Figure 1B:
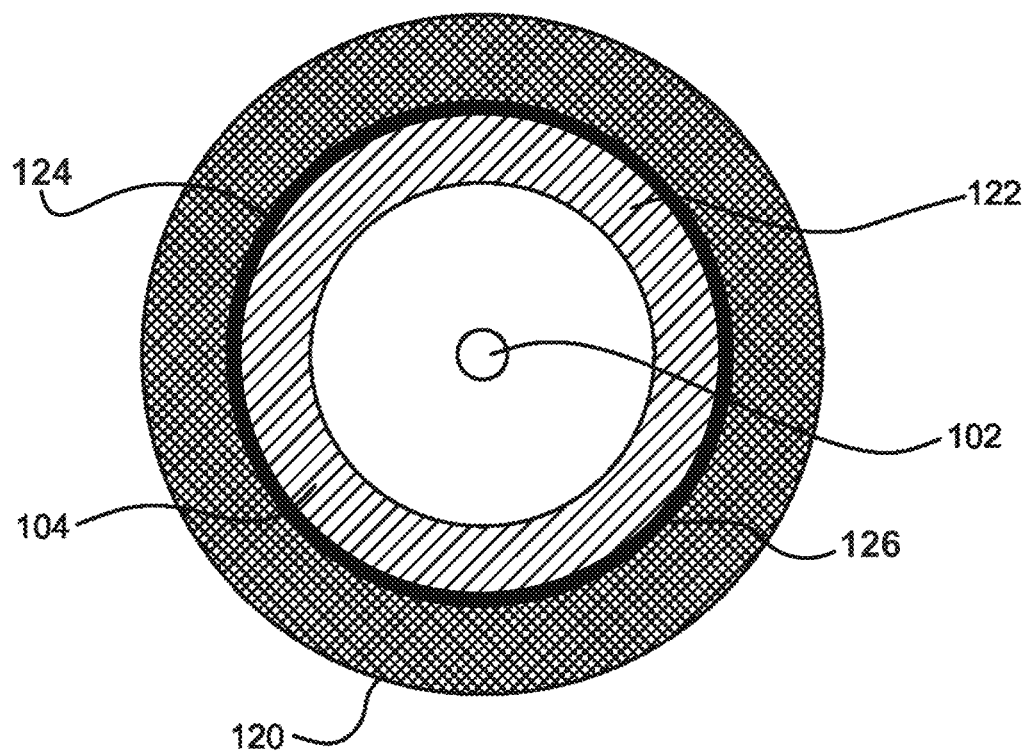

With initial reference to FIG. 1B, balloon 104 of FIG. 1A can further comprise a structural layer 122. Structural layer 122 can comprise any material that can be expanded to accommodate expansion of balloon 104. These materials include, but are not limited to expanded polytetrafluoroethylene (ePTFE), other fluoropolymers, expanded polyethylene, polyvinylchloride, polyurethane, silicone, polyethylene, polypropylene, polyurethane, polyglycolic acid, polyesters, polyamides (such as nylon 12, nylon 11, nylon 9, nylon 6/9 and nylon 6/6), polyolefins, polyether block amides, polyimides, polycarbonates, polyphenylene sulfides, polyphenylene oxides, polyethers, silicones, styrenic polymers, copolymers thereof, and mixtures thereof. As used herein, the term "copolymer" shall be used to refer to any polymer formed from two or more monomers, e.g. 2, 3, 4, 5 and so on and so forth.

Examples of some copolymers of such materials include the polyether-block-am ides, available from Elf Atochem North America in Philadelphia, Pa. under the tradename of PEBAX®. Another suitable copolymer is a polyetheresteramide. Suitable polyester copolymers include, for example, polyethyelene terephthalate and polybutylene terephthalate, polyester ethers and polyester elastomer copolymers such as those available from DuPont in Wilmington, Del. under the tradename of HYTREL®.

Block copolymer elastomers such as those copolymers having styrene end blocks, and midblocks formed from butadiene, isoprene, ethylene/butylene, ethylene/propene, and so forth can be employed herein. Other styrenic block copolymers include acrylonitrile-styrene and acrylonitrile-butadiene-styrene block copolymers. Also, block copolymers wherein the particular block copolymer thermoplastic elastomers in which the block copolymer is made up of hard segments of a polyester or polyamide and soft segments of polyether can also be employed herein.

In various embodiments, the surface(s) or outward configuration of structural layer 122 can be modified with textures, folds, flaps, invaginations, corrugations, protrusions, spikes, scorers, depressions, grooves, pores, coatings, particles, and the like or combinations thereof. Such depressions, grooves, and/or pores can be used increase the effective surface area over which the coating can be placed. This may assist in reducing the overall length or profile of medical device and/or balloon 104.

In various embodiments, structural layer 122 can provide a uniform tube to be coated at a first state which will concentrically/uniformly expand up to a second state. In contrast, conventional Percutaneous Transluminal Angioplasty (PTA) balloons are often coated at second state (in their molded shape) and then compacted to a first state. Structural layer 122 can be coated separate from medical device delivery system 100 or balloon 104 on a mandrel, and later assembled onto balloon 104 with increased manufacturing yields, lower costs, and higher uniformity. As will be described in greater detail, a coating on said structural layer 122 will be covered by delivery sheath 120.

Balloon 104 and/or structural layer 122 can be configured to deliver a therapeutic agent to a vascular site using consistent "on-demand" delivery. For example, balloon 104 can comprise a coating 124. As used herein, the term "coating" refers to one or more materials disposed on the surface of a substrate. Coating 124 can be disposed completely on the surface of balloon 104. Coating 124 can also be disposed, in whole or in part, within the openings or pores present in structural layer 122.

In various embodiments, structural layer 122 can serve as a substrate for uniformly applying coating 124 to balloon 104. Since some balloon materials may not be conducive to being uniformly coated, structural layer 122 can serve as a scaffold to achieve a uniform coating 124. In addition, if structural layer 122 comprises an elastomer, structural layer 122 may assist with recompaction of the underlying balloon (see, e.g., U.S. Pat. No. 6,120,477, Campbell, et al., which is hereby incorporated by reference in its entirety for all purposes). Further, structural layer 122 can be coated with coating 124 prior to placement on elongate member 102. With such a pre-fabricated, coated structural layer 122, any balloon can be converted to a balloon 104 of the present disclosure. Thus, various embodiments comprise placing structural layer 122 on any "off the shelf balloon" or OEM balloon to convert the OEM balloon into balloon 104 of the present disclosure.

Coating 124 may comprise an excipient such as, for example, a paclitaxel-excipient solid composition. For example, paclitaxel is sold commercially in formulations for the treatment of various cancers and for the prevention and treatment of restenosis. Paclitaxel is known to exist in several different physical forms, including amorphous, glassy and crystalline forms, wherein the crystalline forms can be further differentiated into a number of different polymorphs. Furthermore, crystalline paclitaxel can exist as an anhydrate or in hydrated form. The accepted melting point of crystalline paclitaxel is circa 220° C., depending on the heating conditions and polymorph form (Liggins et al. "Solid-state characterization of paclitaxel", J. Pharm. Sci. 1997, Vol. 86, pages 1458-1463). It is known that the particular form of paclitaxel can affect the physical properties of the drug when in solid form. In particular, the adherence of paclitaxel to a surface may be influenced by its physical form, as can its rate of dissolution from a surface to the surroundings. Thus, the effect of formulating paclitaxel in solid form with an excipient cannot easily be predicted.

The excipient of coating 124 can comprise, for example, p-am inobenzoic acid, saccharin, ascorbic acid, methyl paraben, caffeine, calcium salicylate, pentetic acid, creatinine, ethylurea, acetaminophen, aspirin, theobromine, tryptophan, succinic acid, glutaric acid, adipic acid, theophylline, saccharin sodium, amino alcohols, hydroxyl carboxylic acid, ester, anhydrides, hydroxyl ketone, hydroxyl lactone, hydroxyl ester, sugar phosphate, sugar sulfate, ethyl oxide, ethyl glycols, amino acids, peptides, proteins, sorbitan, glycerol, polyalcohol, phosphates, sulfates, organic acids, esters, salts, vitamins, combinations of amino alcohol and organic acid, and their substituted molecules. Further, the excipient can comprise a surfactant chosen from ionic, nonionic, aliphatic, and aromatic surfactants, including PEG fatty esters, PEG omega-3 fatty esters, ether, and alcohols, glycerol fatty esters, sorbitan fatty esters, PEG glyceryl fatty esters, PEG sorbitan fatty esters, sugar fatty esters, PEG sugar esters and derivatives thereof.

Coating 124 can further comprise an additive such as, for example, a chemical compound having one or more hydroxyl, amino, carbonyl, carboxyl, acid, amide, and ester groups. Such additives may be hydrophilic. In various embodiments, the additive is a combination of a surfactant and a chemical compound with one or more hydroxyl, amino, carbonyl, carboxyl, acid, amide, or ester groups. In another embodiment, the additive is a combination of an amino alcohol and an organic acid. The additive may also comprise hydroxyl ketone, hydroxyl lactone, hydroxyl acid, hydroxyl ester, or hydroxyl amide; gluconolactone or ribonic acid lactone; meglumine/lactic acid, meglumine/gentisic acid, meglumine/acetic acid, lactobionic acid, polyethylene glycol sorbitan monolaurate (Tween 20/sorbitol), Tween 20/lactobionic acid, Tween 20/sugar or sugar derivatives, and N-octanoyl N-methylglucamine; a vitamin or derivative thereof; an amino acid or derivative thereof; a protein or derivative thereof; or an albumen. The additive may be soluble in an aqueous solvent and is soluble in an organic solvent. In various embodiments, the additive is an organic acid or an anhydride thereof. In other embodiments, the additive is chosen from sorbitan oleate and sorbitan fatty esters.

In various embodiments, an additive of coating 124 may comprise a hydrophilic part and a drug affinity part, wherein the additive is chosen from p-isononyl phenoxypolyglycidol, PEG laurate, PEG oleate, PEG stearate, PEG glyceryllaurate, Tween 20, Tween 40, Tween 60, PEG glyceryl oleate, PEG glyceryl stearate, polyglyceryllaurate, plyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-β-D-glucopyranoside, n-decyl-β-D-maltopyranoside, n-dodecyl-β-D-glucopyranoside, n-dodecyl-β-D-maltoside, heptanoyl-N-methylglucamide, n-heptyl-β-D-glucopyranoside, n-heptyl-β-D-thioglucoside, n-hexyl-β-D-glucopyranoside, nonanoyi-N-methylglucamide, n-noyl-β-D-glucopyranoside, octanoyl-Nmethylglucamide, n-octyl-β-D-glucopyranoside, octyl-β-D-thioglucopyranoside; cystine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride; succinic anhydride, diglycolic anhydride, glutaric anhydride, acetiamine, benfotiamine, pantothenic acid, cetotiamine, cycothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U (S-methylmethionine); albumin, immunoglobulins, caseins, hemoglobins, lysozymes, immunoglobins, a-2-macroglobulin, fibronectins, vitronectins, firbinogens, lipases, benzalkonium chloride, benzethonium chloride, docecyl trimethyl ammonium bromide, sodium docecylsulfates, dialkyl methylbenzyl ammonium chloride, and dialkylesters of sodium sulfonsuccinic acid; L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propy14-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerols, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol), and penta(propylene glycol), poly(propylene glycol) oligomers, and derivatives and combinations thereof.

In various embodiments, the excipient of coating 124 is an organic additive. For example, the organic additive may comprise at least one of p-aminobenzoic acid, saccharin, ascorbic acid, methyl paraben, caffeine, calcium salicylate, pentetic acid, creatinine, ethylurea, acetaminophen, aspirin, theobromine, tryptophan, succinic acid, glutaric acid, adipic acid, theophylline, and saccharin sodium. Suitably the (at least one) organic additive is independently selected from the list consisting of p-aminobenzoic acid, methyl paraben, caffeine, calcium salicylate and succinic acid. In one embodiment the organic additive is succinic acid. In another embodiment, the organic additive is caffeine. Suitably the (at least one) organic additive is independently selected from the list consisting of p-aminobenzoic acid, methyl paraben, caffeine, calcium salicylate and succinic acid. In one embodiment the organic additive is succinic acid.

In various embodiments, coating 124 can be analysed by ultra-performance liquid chromatography (UPLC) and/or by mass spectrometry to determine the amount of paclitaxel in the coating layer or composition. When the weight % of paclitaxel in the solid coating is known, as in the case of a binary coating layer or composition (i.e. paclitaxel+one organic additive only) then the weight % of the organic additive can easily be determined as being 100—paclitaxel wt %.

In one embodiment, the weight % of therapeutic agent i.e. paclitaxel in coating 124 is between about 5 wt. % and about 95 wt. %, for example between about 10 wt. % and about 95 wt. %, between about 20 wt. % and about 95 wt. %, between about 30 wt. % and about 90 wt. %, between about 45 wt. % and about 85 wt. %, between about 55 wt. % and about 70 wt. %, between about 40 wt. % and about 80 wt. %, between about 25 wt % and about 95 wt.%, between about 30 wt.% and about 85 wt. %, between about 70 wt. % and about 95 wt. %, 70 wt. % and about 80 wt. % or between about 75 wt. % and about 80 wt. %.

In one embodiment, the organic additive is PABA and the weight % of paclitaxel in coating 124 is between about 30 wt. % and about 90 wt. %, for example between about 40 wt. % and about 80 wt. %. In one embodiment, the organic additive is PABA and the ratio (wt. %) of paclitaxel:PABA in the solid composition or coating layer is between about 3:7 and about 9:1, for example between about 2:3 and about 4:1.

In one embodiment, the organic additive is methyl paraben and the weight % of paclitaxel in coating 124 is between about 45 wt. % and about 85 wt. %, for example between about 55 wt. % and about 70 wt. %. In one embodiment, the organic additive is methyl paraben and the ratio (wt. %) of paclitaxel:methyl paraben in the solid composition or coating layer is between about 4:5 and about 9:1, for example between about 1:1 and about 7:3.

In one embodiment, the organic additive is caffeine and the weight % of paclitaxel in coating 124 is between about 70 wt. % and about 95 wt. %, for example between about 75 wt. % and about 90 wt. %. In one embodiment, the organic additive is caffeine and the ratio (wt. %) of paclitaxel:caffeine in the solid composition or coating layer is between about 7:3 and about 95:5, for example between about 3:1 and about 9:1 wt. %.

In one embodiment, the organic additive is calcium salicylate and the weight % of paclitaxel in coating 124 is between about 70 wt. % and about 90 wt. %, for example between about 75 wt. % and about 80 wt. %. In one embodiment, the organic additive is calcium salicylate and the ratio (wt. %) of paclitaxel:calcium salicylate in the solid composition or coating layer is between about 7:3 and about 9:1, for example between about 3:1 and about 4:1.

In one embodiment, the organic additive is succinic acid and the weight % of paclitaxel in coating 124 is between about 70 wt. % and about 90 wt. %, for example between about 75 wt. % and about 85 wt. %. In one embodiment, the organic additive is succinic acid and the ratio (wt. %) of paclitaxel:succinic acid in the solid composition or coating layer is between about 7:3 and about 9:1, for example between about 3:1 wt. % and about 6:1.

In one embodiment the organic additive is selected from the group consisting of p-aminobenzoic acid (PABA), saccharin, ascorbic acid, methyl paraben, caffeine, calcium salicylate, pentetic acid, creatinine, ethylurea, acetaminophen, aspirin, theobromine, tryptophan, succinic acid, glutaric acid, adipic acid, theophylline, and saccharin sodium, and weight % of paclitaxel in the solid composition or coating layer is between about 30 wt. % and about 90 wt. %, such as between about 50 wt. % and about 90 wt. %.

In one embodiment the organic additive is selected from the group consisting of p-aminobenzoic acid, saccharin, ascorbic acid, methyl paraben, caffeine, calcium salicylate, pentetic acid, creatinine, ethylurea, acetaminophen, aspirin, theobromine, tryptophan, succinic acid, glutaric acid, adipic acid, theophylline, and saccharin sodium, and the ratio (wt. %) of paclitaxel:organic additive is between about 3:7 and about 9:1, such as between about 1:1 and about 9:1.

In one embodiment the organic additive is selected from the group consisting of p-aminobenzoic acid, methyl paraben, caffeine, calcium salicylate and succinic acid, and the weight % of paclitaxel in the solid composition or coating layer is between about 30 wt. % and about 90 wt. %, such as between about 50 wt. % and about 90 wt. %.

In one embodiment the organic additive is selected from the list consisting of p-aminobenzoic acid, methyl paraben, caffeine, calcium salicylate and succinic acid and the ratio (wt. %) of paclitaxel:organic additive is between about 3:7 and about 9:1, such as between about 1:1 and about 9:1.

In one embodiment, the organic additive is tris (hydroxymethyl)-methylammonium stearate and the weight % of paclitaxel in coating is between about 80 wt. % and about 99 wt. %.

In various embodiments, coating 124 can further comprise a hydrophilic coating. Suitable components for the hydrophilic coating include, but are not limited to, ionic surfactants including benzethonium chloride (e.g. HYAMINE®), benzalkonium chloride, cetylpyridinium chloride, cetalkonium chloride, laurtrimonium bromide, myristyltrimethylammonium bromide, cetrimide, cetrimonium bromide, stearalkonium chloride, n,n-diethylnicotinamide, cholesterol, calcium salicylate, methyl salicylate, sodium salicylate, a-tocopherol, thiamine, niacinamide, dimethyl sulfoxide, poloxamers (such as 101, 105, 108, 122, 123, 124, 181, 182, 183, 184, 185, 188, 212, 215, 217, 231, 234, 235, 237, 238, 282, 284, 288, 331, 333, 434, 335, 338, 401, 402, 403, and 407), sorbitan monolaurate, polysorbate 20, polysorbate 40, polysorbate 60, polysorbate 80, polyvinyl alcohol, polyethylene glycol (PEG, molecular weight ranges from 400-50,000, with preferred from 700-15,000), PEG-amine, PEG-modified biopharmaceuticals and/or molecules, PEG amines (that include azido PEG amines and PEG diamines), JEFFAMINES® which are polyoxyalkyleneamines, quartenary ammonium compounds, 1,2-ditetradecanoyl-sn-glycero-3-phosphocholine, 1,2-dimyristoyl-sn-glycero-3-phospho-rac-(1-glycerol), 1,2-dimyristoyl-sn-glycero-3-phosphocholine, polypropylene glycol, heparin, or heparin derivatives, dextran, agarose, inclusion complexes such as cyclic oligosaccharides like cyclodextrin and its derivatives, including hydroxypropyl-β-cyclodextrin (HPβCD), Captisol® (a trademark of CyDex Pharmaceuticals, Inc.), dimethyl-β-cyclodextrin, α-cyclodextrin (αCD), alginate, polyacrylamide, polyglycidol, poly(vinyl alcohol-co-ethylene), poly(ethyleneglycol-co-propyleneglycol), poly(vinyl acetate-co-vinyl alcohol), poly(tetrafluoroethylene co-vinyl alcohol), poly(acrylonitrile-co-acrylamide), poly (acrylonitrile-co-acrylic acid-co-acrylamide), polyacrylic acid, poly-lysine, polyethyleneimine, polyvinyl pyrrolidone, polyhydroxyethylmethacrylate, cyclodextrins, γ-cyclodextrin, sulfobutylether-β-cyclodextrin, and polysulfone, polysaccharides and their copolymers, shellolic acid, ipromide, urea, either alone or in combination. Other coatings are known in the art, see, e.g., U.S. Patent Publication 20100233266, which is hereby incorporated by reference in its entirety for all purposes, can also be used as part of this invention. In another embodiment, coating 124 is a heparin coating, such those described in U.S. Pat. Nos. 4,810,784 and 6,559,131.

Coating 124 can further comprise, for example, at least one therapeutic agent 126. A "therapeutic agent" as used herein, which is used interchangeable with the term "drug", is an agent that induces a bioactive response. Such agents include, but are not limited to, cilostazol, everolimus, dicumarol, zotarolimus, carvedilol, anti-thrombotic agents such as heparin, heparin derivatives, urokinase, and dextrophenylalanine proline arginine chloromethylketone; antiinflammatory agents such as dexamethasone, prednisolone, corticosterone, budesonide, estrogen, sulfasalazine and mesalamine, sirolimus and everolimus (and related analogs), anti-neoplastic/antiproliferative/anti-miotic agents such as major taxane domain-binding drugs, such as paclitaxel and analogues thereof, epothilone, discodermolide, docetaxel, paclitaxel protein-bound particles such as ABRAXANE(R) (ABRAXANE is a registered trademark of ABRAXIS BIOSCIENCE, LLC), paclitaxel complexed with an appropriate cyclodextrin (or cyclodextrin like molecule), rapamycin and analogues thereof, rapamycin (or rapamycin analogs) complexed with an appropriate cyclodextrin (or cyclodextrin like molecule), 17β-estradiol, 17β-estradiol complexed with an appropriate cyclodextrin, dicumarol, dicumarol complexed with an appropriate cyclodextrin, β-lapachone and analogues thereof, 5-fluorouracil, cisplatin, vinblastine, cladribine, vincristine, epothilones, endostatin, angiostatin, angiopeptin, monoclonal antibodies capable of blocking smooth muscle cell proliferation, and thymidine kinase inhibitors; lytic agents; anaesthetic agents such as lidocaine, bupivacaine and ropivacaine; anti-coagulants such as D-Phe-Pro-Arg chloromethyl ketone, an RGD peptide-containing compound, AZX100 a cell peptide that mimics HSP20 (Capstone Therapeutics Corp., USA), heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, a) functional molecules consisting of a growth factor and a cytotoxin, b) functional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; agents that interfere with endogenous vasoactive mechanisms; inhibitors of leukocyte recruitment, such as monoclonal antibodies; cytokines; hormones, radiopaque agents such as iodinated contrast agents, gold, or barium, or a combination thereof. Suitably an additional coating layer comprises heparin.

In various embodiments, coating 124 comprises at least one hydrophilic component that raises the solubility point of a hydrophobic therapeutic agent 126. As used herein, the term "raises the solubility point of a hydrophobic therapeutic agent" means that there is an increase of concentration of a hydrophobic therapeutic agent 126 at least 10% above the maximum solubility for therapeutic agent 126 in neat DI-water at room temperature and standard atmospheric conditions. This is usually due to the presence of an additional agent that allows for enhanced solubility (i.e., a hydrophilic component in coating 124). This still allows for a portion of therapeutic agent 126 to not be dissolved into the water. For example, paclitaxel at room temperature in neat DI-water has a solubility limit of about 0.4 $\mu$M. The addition of hydroxypropyl-β-cyclodextrin at a concentration of 60% (w/v in water) raises the solubilized concentration of paclitaxel in solution to approximately 4 mM, well above a 10% increase in solubility (Sharma et al., Journal of Pharmaceutical Sciences 84, 1223 (1995)).

In various embodiments, a hydrophobic therapeutic agent 126 is sequestered by or complexed with one or more solubilizing agents such that when delivered to the intended tissue site the drug dissociates from the solubilizing agent and binds to tissue. Such solubilizing agents are known in the art (see, e.g., U.S. Patent Publication 20080118544).

Therapeutic agent 126 can be delivered to the tissue in various structural forms, including but not limited to micelles, liposomes, micro-aggregates, nanospheres, microspheres, nanoparticles, microparticles, crystallites, inclusion complexes, emulsions, gels, foams, creams, suspensions, eutectics, perieutectics, and solutions or any combination thereof. In various embodiments, therapeutic agent 126 is delivered to the tissue in a solubilized form. Therapeutic agent 126 can also be delivered to the tissue in a gel. In other embodiments, therapeutic agent 126 is delivered to the tissue in a solubilized form that precipitates from solution into a solid form. In yet other embodiments, therapeutic agent 126 is delivered to the tissue as a combination of solubilized and solid forms.

Balloon 104 may comprise an adherent layer interposed between coating 124 and structural layer 122. The adherent layer, which is a separate and distinct layer underlying coating 124, may improve the adherence of coating 124 to structural layer 122 and further maintain the integrity of the coating, particularly during transit to the tissue to the be treated. In one embodiment, the adherent layer comprises a polymer, which is suitably biocompatible and avoids irritation of body tissue. Examples of such polymers include, but are not limited to polyolefins, polyisobutylene, ethylene-α-olefin copolymers, acrylic polymers and copolymers, polyvinyl chloride, polyvinyl methyl ether, polyvinylidene fluoride and polyvinylidene chloride, fluoropolymers, e.g. expanded polytetrafluoroethylene (ePTFE), polytetrafluoroethylene (PTFE), fluorinated ethylene-propylene (FEP), perfluorocarbon copolymers, e.g. tetrafluoroethylene perfluoroalkylvinyl ether (TFE/PAVE) copolymers, copolymers of tetrafluoroethylene (TFE) and perfluoromethyl vinyl ether (PMVE), copolymers of TFE with functional monomers that comprise acetate, alcohol, amine, amide, sulfonate, functional groups and the like as described in U.S. Pat. No. 8,658,707 (W. L. Gore and Associates, incorporated herein by reference, as well as combinations thereof), polyacrylonitrile, polyvinyl ketones, polystyrene, polyvinyl acetate, ethylene-methyl methacrylate copolymers, acrylonitrile-styrene copolymers, ABS resins, Nylon 12 and its block copolymers, polycaprolactone, polyoxymethylenes, polyethers, epoxy resins, polyurethanes, rayon-triacetate, cellulose, cellulose acetate, cellulose butyrate, cellophane, cellulose nitrate, cellulose propionate, cellulose ethers, carboxymethyl cellulose, chitins, polylactic acid, polyglycolic acid, polylactic acid-polyethylene oxide copolymers, polyethylene glycol, polypropylene glycol, polyvinyl alcohol, elastomeric polymers such as silicones (e.g., polysiloxanes and substituted polysiloxanes), polyurethanes, thermoplastic elastomers, ethylene vinyl acetate copolymers, polyolefin elastomers, EPDM rubbers and mixtures thereof.

In another embodiment, an additional coating layer comprising a therapeutic agent other than paclitaxel is interposed between coating 124 and structural layer 122. Said coating layer is a separate and distinct layer underlying coating 124 and may provide a therapeutic benefit in addition to the benefit provided by the paclitaxel i.e. allowing for adjunctive therapies to be combined with the paclitaxel-organic additive. For example, a coating of the invention can be applied to a medical device already coated with an immobilized biologically active heparin coating, while maintaining the activity of both coatings (i.e. the anti-proliferative effect of the paclitaxel-organic additive composition and the antithrombin III (ATIII) binding activity of the heparin, as measured by known analytical methods. Thus, coated medical devices of the invention with a heparin bonded undercoating appear to have the added benefit of producing a reduction in sub-acute thrombosis after implantation. In one embodiment, the additional coating layer comprises a therapeutic agent other than paclitaxel. Alternatively, said additional coating layer comprising a therapeutic agent other than paclitaxel will overlay a portion, or all of coating 124. As described above, such coating layer is a separate and distinct layer overlying the paclitaxel-organic additive(s) coating 124.

In one embodiment, the additional coating layer comprises a therapeutic agent 126 selected from cilostazol, everolimus, dicumarol, zotarolimus, carvedilol, anti-thrombotic agents such as heparin, heparin derivatives, urokinase, and dextrophenylalanine proline arginine chloromethylketone; antiinflammatory agents such as dexamethasone, prednisolone, corticosterone, budesonide, estrogen, sulfasalazine and mesalamine, sirolimus and everolimus (and related analogs), anti-neoplastic/antiproliferative/anti-miotic agents such as major taxane domain-binding drugs, such as paclitaxel and analogues thereof, epothilone, discodermolide, docetaxel, paclitaxel protein-bound particles such as ABRAXANE(R) (ABRAXANE is a registered trademark of ABRAXIS BIOSCIENCE, LLC), paclitaxel complexed with an appropriate cyclodextrin (or cyclodextrin like molecule), rapamycin and analogues thereof, rapamycin (or rapamycin analogs) complexed with an appropriate cyclodextrin (or cyclodextrin like molecule), 17β-estradiol, 17β-estradiol complexed with an appropriate cyclodextrin, dicumarol, dicumarol complexed with an appropriate cyclodextrin, β-lapachone and analogues thereof, 5-fluorouracil, cisplatin, vinblastine, cladribine, vincristine, epothilones, endostatin, angiostatin, angiopeptin, monoclonal antibodies capable of blocking smooth muscle cell proliferation, and thymidine kinase inhibitors; lytic agents; anaesthetic agents such as lidocaine, bupivacaine and ropivacaine; anti-coagulants such as D-Phe-Pro-Arg chloromethyl ketone, an RGD peptide-containing compound, AZX100 a cell peptide that mimics HSP20 (Capstone Therapeutics Corp., USA), heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factors, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, Afunctional molecules consisting of a growth factor and a cytotoxin, b (functional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; agents that interfere with endogenous vasoactive mechanisms; inhibitors of leukocyte recruitment, such as monoclonal antibodies; cytokines; hormones, radiopaque agents such as iodinated contrast agents, gold, or barium, or a combination thereof. Suitably an additional coating layer comprises heparin.

In one embodiment, the medical device further comprises a protective top coat overlying coating 124. The top coat may further minimise loss of the paclitaxel-excipient of coating 124 before it is brought into contact with target tissues, for example during device assembly and packaging, transit to the site to be treated, or if the device is a balloon or stent, during the first moments of inflation or expansion before coating layer is pressed into direct contact with target tissue. The top coat may be of particular use during crush loading, for example when an expandable medical device such as a balloon, stent, stent-graft or graft is coated in its expanded form, before being contracted into its non-expanded form. The contracted form of the coated device will usually be stored for a period of time before use. A top coating may prevent loss of the coating 124 during storage and during expansion when the device is deployed. Alternatively, or additionally, the top coat may have lubricious properties to reduce frictional forces on the device while in transit. Suitably the top coat is degradable or soluble and will release slowly in the body lumen while protecting the drug layer. The top layer will erode more slowly if it is comprised of more hydrophobic, high molecular weight additives. Surfactants are examples of more hydrophobic structures with long fatty chains, such as Tween 20 and polyglyceryl oleate. High molecular weight additives include polyethylene oxide, polyethylene glycol, and polyvinyl pyrrolidone. Hydrophobic drug itself can act as a top layer component. For example, paclitaxel or rapamycin are hydrophobic. They can be used in the top layer. On the other hand, the top layer cannot erode too slowly or it might actually slow the release of drug during deployment at the target site. Other additives useful in the top coat include additives that strongly interact with therapeutic agent 126 or coating 124, such as p-isononylphenoxypolyglycidol, PEG laurate, Tween 20, Tween 40, Tween 60, PEG oleate, PEG stearate, PEG glyceryl laurate, PEG glyceryl oleate, PEG glyceryl stearate, polyglyceryl laurate, polyglyceryl oleate, polyglyceryl myristate, polyglyceryl palmitate, polyglyceryl-6 laurate, plyglyceryl-6 oleate, polyglyceryl-6 myristate, polyglyceryl-6 palmitate, polyglyceryl-10 laurate, plyglyceryl-10 oleate, polyglyceryl-10 myristate, polyglyceryl-10 palmitate PEG sorbitan monolaurate, PEG sorbitan monolaurate, PEG sorbitan monooleate, PEG sorbitan stearate, PEG oleyl ether, PEG laurayl ether, octoxynol, monoxynol, tyloxapol, sucrose monopalmitate, sucrose monolaurate, decanoyl-N-methylglucamide, n-decyl-[beta]-D-glucopyranoside, n-decyl-[beta]-D-maltopyranoside, n-dodecyl-[beta]-D-glucopyranoside, n-dodecyl-[beta]-D-maltoside, heptanoyl-N-methylglucamide, n-heptyl-[beta]-

D-glucopyranoside, n-heptyl-[beta]-D-thioglucoside, n-hexyl-[beta]-D-glucopyranoside, nonanoyl-N-methylglucamide, n-noyl-[beta]-D-glucopyranoside, octanoyl-N-methylglucamide, n-octyl-[beta]-D-glucopyranoside, octyl-[beta]-D-thioglucopyranoside; cysteine, tyrosine, tryptophan, leucine, isoleucine, phenylalanine, asparagine, aspartic acid, glutamic acid, and methionine; acetic anhydride, benzoic anhydride, ascorbic acid, 2-pyrrolidone-5-carboxylic acid, sodium pyrrolidone carboxylate, ethylenediaminetetraacetic dianhydride, maleic and anhydride, succinic anhydride, diglycolic anhydride, glutaric anhydride, acetiamine, benfotiamine, pantothenic acid; cetotiamine; cyclothiamine, dexpanthenol, niacinamide, nicotinic acid, pyridoxal 5-phosphate, nicotinamide ascorbate, riboflavin, riboflavin phosphate, thiamine, folic acid, menadiol diphosphate, menadione sodium bisulfite, menadoxime, vitamin B12, vitamin K5, vitamin K6, vitamin K6, and vitamin U; albumin, immunoglobulins, caseins, hemoglobins, lysozymes, immunoglobins, a-2-macroglobulin, fibronectins, vitronectins, fibrinogens, lipases, benzalkonium chloride, benzethonium chloride, docecyl trim ethyl ammonium bromide, sodium docecylsulfates, dialkyl methylbenzyl ammonium chloride, and dialkylesters of sodium sulfosuccinic acid, L-ascorbic acid and its salt, D-glucoascorbic acid and its salt, tromethamine, triethanolamine, diethanolamine, meglumine, glucamine, amine alcohols, glucoheptonic acid, glucomic acid, hydroxyl ketone, hydroxyl lactone, gluconolactone, glucoheptonolactone, glucooctanoic lactone, gulonic acid lactone, mannoic lactone, ribonic acid lactone, lactobionic acid, glucosamine, glutamic acid, benzyl alcohol, benzoic acid, hydroxybenzoic acid, propyl 4-hydroxybenzoate, lysine acetate salt, gentisic acid, lactobionic acid, lactitol, sinapic acid, vanillic acid, vanillin, methyl paraben, propyl paraben, sorbitol, xylitol, cyclodextrin, (2-hydroxypropyl)-cyclodextrin, acetaminophen, ibuprofen, retinoic acid, lysine acetate, gentisic acid, catechin, catechin gallate, tiletamine, ketamine, propofol, lactic acids, acetic acid, salts of any organic acid and organic amine, polyglycidol, glycerol, multiglycerols, galactitol, di(ethylene glycol), tri(ethylene glycol), tetra(ethylene glycol), penta(ethylene glycol), poly(ethylene glycol) oligomers, di(propylene glycol), tri(propylene glycol), tetra(propylene glycol), and penta(propylene glycol), poly(propylene glycol) oligomers, a block copolymer of polyethylene glycol and polypropylene glycol, PTFE, ePTFE and derivatives and combinations thereof.

In various embodiments coating 124 can be formed into a structural component that is combined with balloon 104. Such constructs eliminate the requirement for structural layer 122 per se, yet fully preserve the key functions provided by coating 124. Such constructs may also improve manufacturability and can be combined with most any expandable member, such as a balloon. For example, where medical device 104 comprises a balloon, a tubular form can be cast or otherwise formed from one or more materials of the described coating and disposed over balloon 104 prior to placement of the delivery sheath 120. In one embodiment such tubular forms would be made by solvating the coating material(s) into a viscous state and through processes known to the art such as gel extrusion, casting, molding or solution casting/forming formed into the desired tubular shape. The solvent(s) used are subsequently removed to dry or partially dry the tube and makes it easy to dispose over balloon 104.

In various embodiments, coating 124 can render balloon 104 very rigid. Due to its rigidity, balloon 104 may be difficult to track through tortuous anatomy. Thus, in one embodiment, after applying coating 124 to structural layer 122 and/or balloon 104, the delivery sheath 120 is slipped over structural layer 122 and/or balloon 104 and coating 124 cracked by bending and/or twisting structural layer 122 and/or balloon 104. This may improve the conformability of balloon 104 while preventing particulates from escaping delivery sheath 120 prior to treatment. In other embodiments, instead of fully coating structural layer 122 and/or balloon 104, coating 124 is applied as "rings" such that in between said "rings" structural layer 122 and/or balloon 104 is conformable, which may allow structural layer 122 and/or balloon 104 to bend or flex at the uncoated regions. In yet other embodiments, rather than "rings", coating 124 can be applied to structural layer 122 and/or balloon 104 as an extruded, helically laid-down, continuous beading. In further embodiments, coating 124 can be applied to structural layer 122 and/or balloon 104 as discrete dots or other shapes or discrete patterns.

Coating 124 can, for example, be applied to structural layer 122 and/or balloon 104 in a discontinuous fashion. For example, the amount or thickness of coating 124 can be varied over the surface of the substrate. In instances where drug delivery is desired only at the proximal and distal ends of a stent, for example, coatings 124 applied to only the proximal and distal portions of structural layer 122 and/or balloon 104 may be desirable, especially for treatment or prevention of stent end stenosis. Coating 124 can similarly vary over the area of structural layer 122 and/or balloon 104.

As previously described, in various embodiments, medical device 104 is surrounded by an expandable delivery sheath 120. Delivery sheath 120 can, for example, prevent medical device 104 from substantially eluting or releasing coating 124 and/or therapeutic agent 126 into the blood stream of a patient during tracking and delivery of medical device 104 to a desired treatment area.

Delivery sheath 120 can comprise, for example, a non- or semi-porous polymeric material. For example, delivery sheath 120 can comprise, among other materials, PTFE, including expanded PTFE (ePTFE), fluoropolymers, expanded polyethylene, polyvinylchloride, polyurethane, silicone, polyethylene, polypropylene, polyurethane, polyglycolic acid, polyesters, polyam ides (such as nylon 12, nylon 11, nylon 9, nylon 6/9 and nylon 6/6), polyolefins, polyether block amides, polyimides, polycarbonates, polyphenylene sulfides, polyphenylene oxides, polyethers, silicones, styrenic polymers, copolymers thereof, and mixtures thereof. As used herein, the term "copolymer" shall be used to refer to any polymer formed from two or more monomers, e.g. 2, 3, 4, 5 and so on and so forth. Examples of some copolymers of such materials include the polyether-block-amides, available from Elf Atochem North America in Philadelphia, Pa. under the tradename of PEBAX®.

In various embodiments, delivery sheath 120 can comprise a distensible polymeric material such as, for example, particular forms of ePTFE. Further, delivery sheath 120 comprises a highly oriented polymeric material. For example, delivery sheath 120 can comprise a polymeric material having highly oriented nodes. Delivery sheath 120 can comprise such a highly oriented film wrapped to form a tubular structure. In other embodiments, delivery sheath 120 can comprise an extruded polymeric tube such as, for example, an extruded ePTFE tube.

Figure 2A:
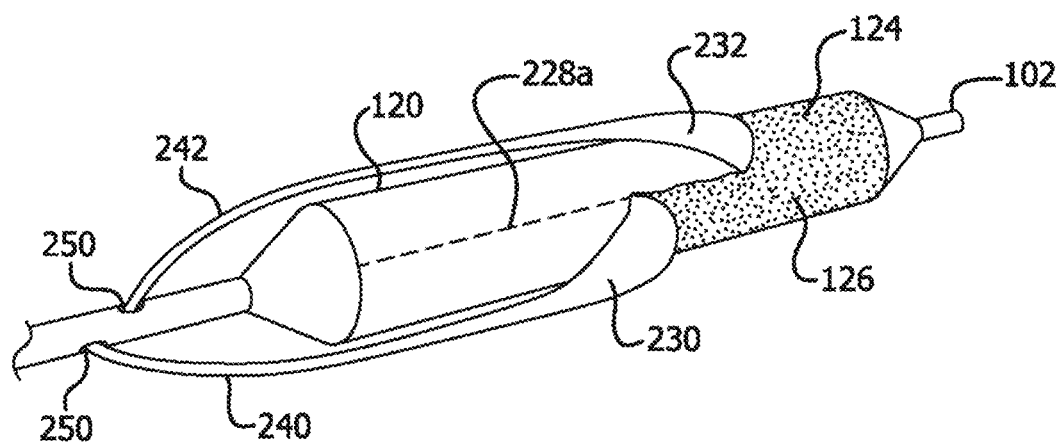
FIGS. 2A and 2B illustrate perspective views of a medical device delivery system in accordance with the present disclosure.
Figure 2B:
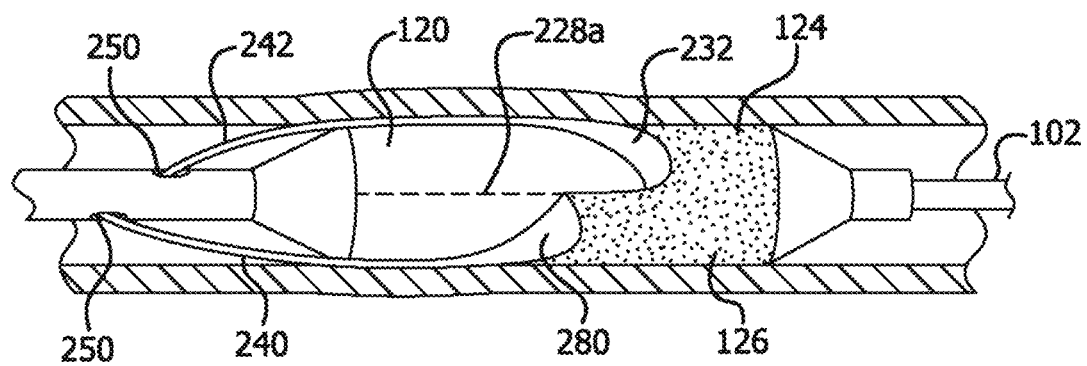

In various embodiments, delivery sheath 120 comprises a sheath configured to be removed from balloon 104 by peeling back two or more segments. With initial reference to FIGS. 2A and 2B, delivery sheath 120 can comprise a first split line 228a and a second split line 228b. For example, first split line 228a and second split line 228b can comprise a line along which delivery sheath 120 will split when tension is applied to the delivery sheath at a particular position in a specific direction, such that the sleeve can be split along split lines 228a and 228b. In various embodiments, delivery sheath 120 comprises a highly oriented film such that first split line 228a and 228b represent lines along which the film will "naturally" split when tension is applied. For example, a "natural" split line within a film may align along a direction of orientation of nodes and fibrils within the material. In various embodiments, the nodes and fibrils of the material of delivery sheath 120 are oriented such that split lines 228a and 228b are relatively parallel to catheter 102. Although described in connection with two split lines, delivery sheath 120 can comprise any number of split lines.

Split lines 228a and 228b can comprise, for example, relatively straight lines which travel in a longitudinal direction between the distal and proximal ends of delivery sheath 120. In other embodiments, split lines 228a and 228b can comprise non-linear lines, such as curved or spiral lines, that travel in a generally longitudinal direction between the distal and proximal ends of delivery sheath 120. Although described with reference to specific shapes and configurations (e.g., linear, curved, spiral), split lines 228a and 228b can comprise lines of any shape and configuration.

Delivery sheath 120 can further comprise, for example, a first segment 230 and a second segment 232. In various embodiments, first segment 230 comprises a portion of delivery sheath 120 between first split line 228a and second split line 228b. In various embodiments, second segment 232 can comprise another portion of delivery sheath 120 between first split line 228a and second split line 228b and opposite first segment 230. In various embodiments, first segment 230 and second segment 232 comprise similar shapes and configurations. For example, in embodiments in which first split line 228a and second split line 228b comprise relatively longitudinal lines that extend along the length of delivery sheath 120, first segment 230 and second segment 232 comprise similar or identical segments. Stated another way, in various embodiments, first split line 228a and second split line 228b bisect delivery sheath 120 into first segment 230 and second segment 232 having approximately equivalent sizes and shapes. In other embodiments, first segment 230 and second segment 232 can comprise different shapes and sizes. As discussed in connection with first split line 228a and second split line 228b, delivery sheath 120 can comprise any number of segments.

In various embodiments, first segment 230 comprises a first activation line 240. First activation line can be configured, for example, to initiate and control a tear or split along first split line 228a and/or second split line 228b. For example, when removal of delivery sheath 120 is desired, first activation line 240 can be pulled, causing first split line 228a and second split line 228b to tear, which in turn permits first segment 230 to separate from delivery sheath 120 and peel back towards proximal end 106 of elongate member 102. First activation line 240 can comprise, for example, a string, thread, ribbon, or wire attached to an end of first segment 230. In other embodiments, first activation line 240 comprises a tapered or elongated portion of first segment 230. Any configuration of first activation line 240 capable of peeling back first segment 230 is within the scope of the present disclosure.

In various embodiments, first activation line 240 travels from proximal end 106 of elongate member 102 towards distal end 108, exiting elongate member 102 through a first portal 350. As first activation line 240 is pulled towards proximal end 106 of elongate member 102, first segment 230 is peeled away from the outer surface of balloon 104 along first split line 228a and second split line 228b, exposing a portion of balloon 104.

Similarly to first activation line 240, second activation line 242 can be pulled towards proximal end 106 of elongate member 102 to peel away second segment 232 from balloon 104. In various embodiments, second activation line 242 is activated after first activation line 240. This is to avoid full eversion of outer delivery sheath 120. Full eversion occurs when the entire diameter of a sheath or sleeve is everted from one end of a balloon toward the opposite end. In such configurations, the sleeve or sheath remains intact as a single sleeve, and cannot be retracted through portals 350 and/or 252 in the form of sleeve or sheath segments.

In various embodiments, first activation line 240 comprises a shorter length than second activation line 242. In such embodiments, both first activation line 240 and second activation line 242 can be actuated at the same time. Because second activation line 242 is longer than first activation line 240, second segment 232 will begin to peel back after first segment 230. First activation line 240 and second activation line 242 can comprise any configuration that permits first segment 230 and second segment 232 to be peeled back independently from one another.

Figure 3:
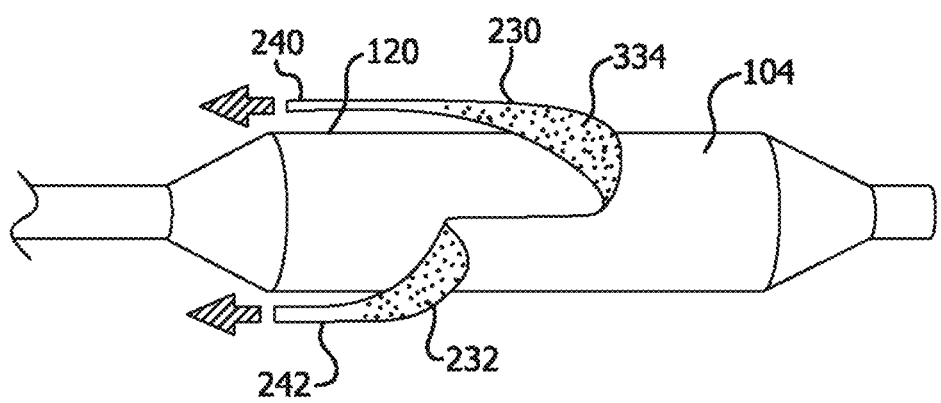
FIG. 3 illustrates a perspective view of a medical device delivery system in accordance with the present disclosure.

With reference to FIG. 3, first segment 230 and/or second segment 232 can further comprise, for example, a surface 334. In various embodiments, surface 334 can comprise textures, protrusions, spikes, scorers, depressions, grooves, coatings, particles, and the like. Surface 334 can, for example, modify tissues into which therapeutic agents will be (or have been) delivered, control placement of the system of the invention, and direct fluid transfer. Further, surface 334 may help in increased transfer of a therapeutic agent onto, more deeply and/or into deeper tissues. In addition, coatings of surface 334 may aid in microscopic wetting of said sheath material. In various embodiments, surface 334 comprises a coating of crosslinked polyvinyl alcohol (see, e.g., U.S. Pat. No. 7,871,659). In another embodiment, said coating of surface 334 can comprise a heparin coating, such as those described in U.S. Pat. Nos. 4,810,784 and 6,559,131, both of which are hereby incorporated by reference herein in their entireties for all purposes.

Figure 4A:
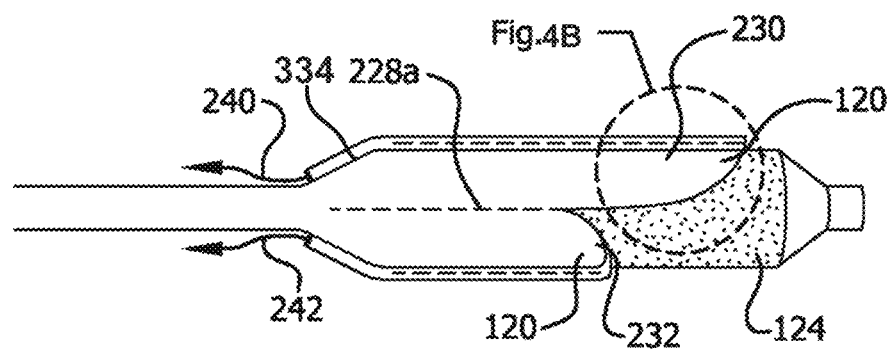
FIGS. 4A and 4B illustrate perspective views of a medical device delivery system in accordance with the present disclosure.
Figure 4B:
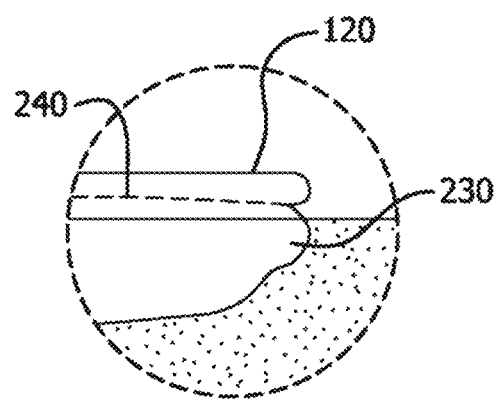

With reference to FIGS. 4A and 4B, activation lines 240 and 242 can be positioned between an inner surface of delivery sheath 120, such as surface 334, and an outer surface of balloon 104. In various embodiments, applying tension to activation lines 240 and 242 can evert first segment 230 and second segment 232 inward, such that the portions travel between surface 334 and the outer surface of balloon 104. This is in contrast to other embodiments in which first segment 230 and second segment 232 are peeled back outwardly and do not travel between surface 334 and outer portion of balloon 104, as illustrated in FIGS. 3A and 3B.

Figure 5A:
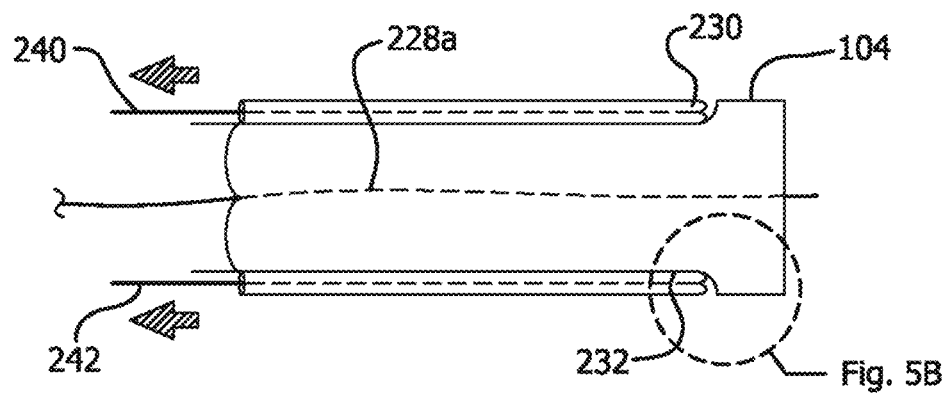
FIGS. 5A and 5B illustrate perspective views of a medical device delivery system in accordance with the present disclosure.
Figure 5B:
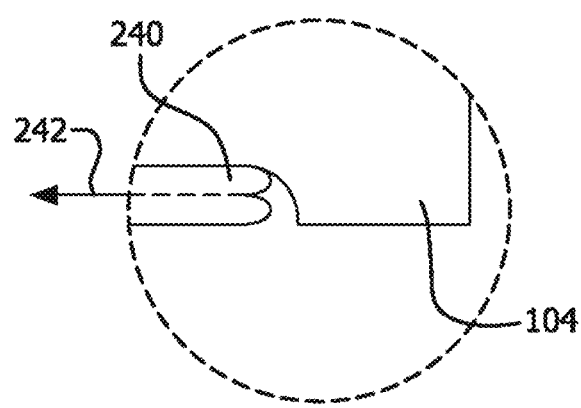
Figure 6A:
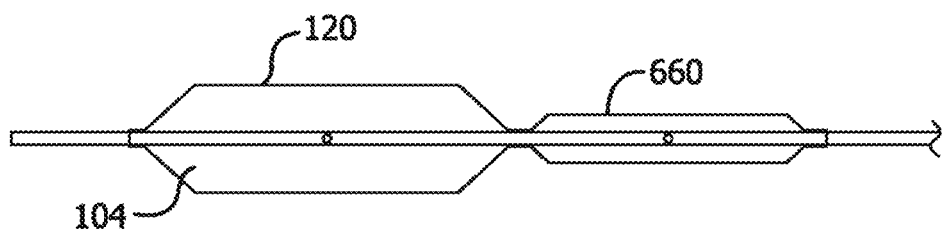
FIGS. 6A-6D illustrate perspective views of a medical device delivery system in accordance with the present disclosure in various stages of deployment.
Figure 6B:
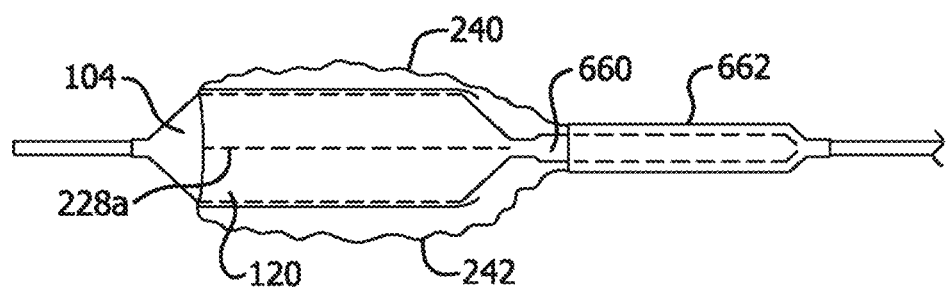
Figure 6C:
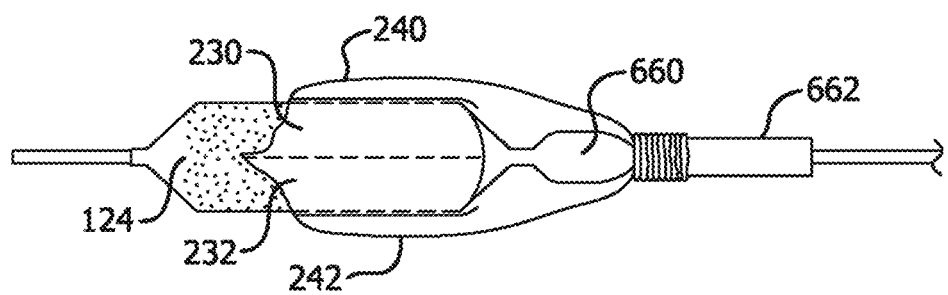
Figure 6D:
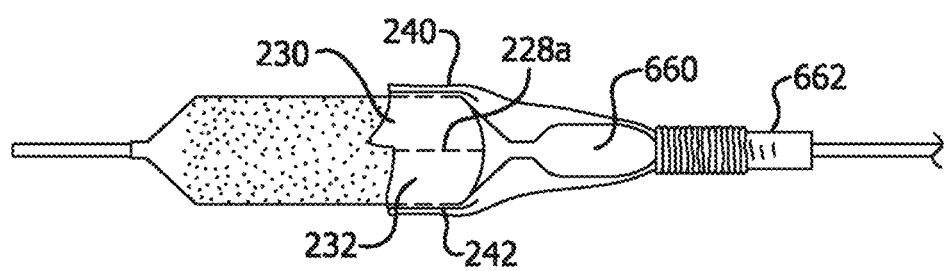

With reference to FIGS. 5A and 5B, activation lines 240 and 242 can be positioned within delivery sheath 120. In various embodiments, activation lines 240 and 242 can be positioned within layers of delivery sheath 120 such that as tension is applied to activation lines 240 and 242, first segment 230 and second segment 232 are peeled within delivery sheath 120. Stated another way, delivery sheath 120 folds in upon itself as first segment 230 and second segment 232 are peeled by activation lines 240 and 242.

With reference to FIGS. 6A-6D, delivery sheath 120 can be converted into first segment 230 and second segment 232 by inflation of a secondary balloon 660. For example, upon sufficient inflation of balloon 104, secondary balloon 660 begins inflation. In various embodiments, secondary balloon 660 comprises a higher compliance than the compliance of balloon 104 such that secondary balloon 660 does not inflate past a desired inflation diameter until balloon 104 is fully inflated. Secondary balloon 660 can be surrounded by a secondary sheath 662. In various embodiments, first activation line 240 and second activation line 242 are attached to secondary sheath 662. In such embodiments, as secondary balloon 660 inflates past a predetermined inflation level, secondary sheath 662 begins to retract, applying tension to first activation line 240 and second activation line 242. This tension causes delivery sheath 120 to split along split lines 228*a* and 228*b* and evert towards secondary balloon 660.

Although described in the preceding paragraphs in connection with specific configurations, any configuration of activation lines 240 and 242 which allows for first segment 230 and second segment 232 to be split, peeled back, and removed from balloon 104 is within the scope of the present disclosure.

In another embodiment, delivery sheath 120 can contain or be marked with radiopaque markers or be constructed to be radiopaque in its entirety. Such radiopaque indicators are used by clinicians to properly track and place an expandable medical device of the invention.

In another embodiment, an expandable device, such as a stent or stent-graft, can be mounted to balloon 104 and delivered to a site within the body where the expandable device is expanded and placed. The advantage of this application is that a therapeutic agent can be delivered to the treatment area at the same time as said expandable device is being delivered. This prevents clinicians from having to switch between a stent delivery balloon and a drug delivery balloon. In one embodiment, the stent is made from a balloon expandable material, such as stainless steel. In another embodiment, the stent is made from a self-expanding material, such as Nitinol. In another embodiment, the stent is made from a biodegradable material, such as a biodegradable polymer, metal or metal alloy. In another embodiment, a stent is attached to a graft. In various embodiments, the graft comprises ePTFE.

Medical device delivery systems of the present disclosure may be suitable for a wide range of applications including, for example, a range of medical treatment applications within the body. Exemplary applications include use as a catheter balloon for transferred drug to or placement or "touch-up" of implanted vascular grafts, stents, stent-grafts, a permanent or temporary prosthesis, or other type of medical implant, treating a targeted tissue within the body, and treating any body cavity, space, or hollow organ passage (s) such as blood vessels, the urinary tract, the intestinal tract, nasal cavity, neural sheath, intervertebral regions, bone cavities, esophagus, intrauterine spaces, pancreatic and bile ducts, rectum, and those previously intervened body spaces that have implanted vascular grafts, stents, prosthesis, or other type of medical implants. Additional examples include balloon used to remove obstructions such as emboli and thrombi from blood vessels, as a dilation device to restore patency to an occluded body passage, as an occlusion device to selectively deliver a means to obstruct or fill a passage or space, and as a centering mechanism for transluminal instruments like catheters. In one embodiment, medical device delivery systems provided by the present disclosure can be used to treat stent restenosis or treat tissue sites where previously placed drug eluting constructs have failed. In another embodiment, medical device delivery systems of the present disclosure can be used to establish or maintain arteriovenous access sites, e.g., those used during kidney dialysis. In one embodiment, delivery systems in accordance with the present disclosure can comprise a medical balloon used for Percutaneous Transluminal Angioplasty (PTA) in patients with obstructive disease of the peripheral arteries. In another embodiment, delivery systems in accordance with the present disclosure can be used to treat coronary stenosis or obstructions.

In other embodiments, delivery systems in accordance with the present disclosure can be applied in configurations other than those which are radially circular. For example, such systems can be used in conjunction with planar devices such as wound dressings, implantable patches (including vascular and hernia patches), transdermal patches, filters, various device delivery components, occluders, and orthopedic implants. In one embodiment, such a system can be incorporated into an implantable lead (e.g., a cardiac or neurostimulation lead), provided the lead is compatible with an expandable member, e.g., features a lumen or pocket into which an expandable member is positionable.

In another embodiment, delivery systems of the present disclosure can be combined with an occlusion device such as a balloon located proximate the device. Said occlusion device may mitigate the movement of drug far from the treatment area. In one embodiment, the bodily fluids isolated by this system can be withdrawn from the body by aspiration prior to removal of the system.

In various embodiments, medical device delivery system 100 can be used to provide treatment to the vasculature of a patient. For example, a method of treatment can comprise advancing an expandable medical device (such as balloon 104) and a radially expandable sheath (such as delivery sheath 120) surrounding at least a portion of the expandable medical device to a treatment area within a patient. Further, the method can comprise applying tension to an activation line (such as first activation line 240 and/or second activation line 242) to split the delivery sheath along two split lines (such as split lines 228*a* and 228*b*) to form a first sheath segment and a second sheath segment (such as first segment 230 and second segment 232). In various embodiments, the method further comprises removing the first sheath segment from the patient. As previously discussed, tension can be applied to the activation lines manually, by a secondary balloon, or in any other suitable manner.

In various embodiments, a method for treating the vasculature of a patient further comprises orienting the expandable medical device subsequent to the step of removing the first sheath segment and prior to the step of removing the second sheath segment from the patient. In such embodiments, the sheath segments are not removed until the device (e.g., balloon 104) is located at a predetermined and desired treatment area within the patient.

In one embodiment, the expanded diameter of balloon 104 is about 4 mm, about 5 mm, about 6 mm, about 7 mm, about 8 mm, about 9 mm, or about 10 mm in diameter with lengths ranging from about 30 to about 150 mm. In another embodiment, the catheter will range in length from about 90 to about 150 cm. In another embodiment, balloon 104 is about 5, 6, 7, 8, 9 or 10 French (Fr) in size before introduction into a body vessel, cavity or duct.

In an embodiment, the removable delivery sheath has at least a portion of the inside layer (luminal facing layer) is textured so as to contact the vessel wall during sheath delivery. In other embodiments, a plurality of removable delivery sheaths are utilized on a balloon and a least one of the plurality of removable delivery sheaths comprises a drug coating. In an embodiment, at least a portion of the inside layer (luminal facing layer) of the removable delivery sheath comprises a drug layer. In various embodiments, removing two of a plurality of removable delivery sheaths comprising a drug coating sufficiently exposes the inside layer of the sheaths in contact with the vessel wall in order to prepare the vessel wall for further medical treatment. In various embodiments, an inside layer (luminal facing layer) of a removable delivery sheath comprises a drug coating and upon inflation of the expandable medical device to a desired inflation diameter, and wherein tension is applied to the activation line, the first sheath segment everts between the first layer of the sheath and the second layer of the sheath to be placed in sufficient contact with the vessel wall as to prepare the vessel wall for further treatment. In another embodiment, an inner surface of a removable delivery sheath comprises a drug coating and whereupon inflation of an expandable medical device to a desired inflation diameter, and wherein tension is applied to the activation line, the first segment everts between the first layer of the sheath and the second sheath layer so as to deliver drug from the inner surface of the sheath to the treatment area.

EXAMPLE 1

This example describes construction of a splitting, retractable balloon cover applied to a medical balloon, in accordance with the present invention.

Expanded polytetrafluoroethylene (ePTFE) film with the following properties was obtained: Width of 120 mm, mass per unit area of about 2.43 g/m2, thickness of about 0.0089 mm, density of about 0.27 g/cc, longitudinal matrix tensile strength of about 649 MPa, transverse matrix tensile strength of about 10.5 MPa, and isopropyl alcohol (IPA) bubble point of about 4.83 kPa.

A stainless steel mandrel measuring 30 cm long and 6.4 mm in diameter was obtained. Five layers of the ePTFE film were wrapped about the mandrel with the ePTFE fibrils generally oriented parallel to the longitudinal direction of the mandrel. The resultant tube of ePTFE measured 120 mm in length.

A second ePTFE film with the following properties was obtained: Width of 25.4 mm, mass per unit area of about 2.66 g/m2, thickness of about 0.0064 mm, density of about 0.42 g/cc, longitudinal matrix tensile strength of about 655 MPa, transverse matrix tensile strength of about 16.6 MPa, and IPA bubble point of about 140.0 kPa.

The second ePTFE film was helically wrapped over the 120 mm ePTFE tube at an angle of 45 degrees to the longitudinal axis of the mandrel, with each successive layer overlapping the previous layer by 50%, such that the 120 mm tube was completely overwrapped. During wrapping, tension was applied such that the second film necked down to a width of about 15 mm as it was applied to the tube. Wrapping continued until there were four layers of film overwrapping the tube.

The overwrapped 120 mm ePTFE tube and mandrel were thermally treated at 380° C. for four minutes. After cooling to room temperature, the second ePTFE film was removed, leaving the original 120 mm tube on the mandrel. After verifying that the tube's film layers were adhered to one another the tube was removed from the mandrel. The ends of the tubes were trimmed to create clean edges.

A non-hydrophilic, percutaneous transluminal angioplasty (PTA) balloon catheter with a 5 mm diameter by 40 mm long nylon balloon was obtained (BMT-035 08QL-504A, Bavaria Medizin Technologie, GmbH). The packaging sleeve supplied on the balloon portion of the catheter was slid proximally off the balloon. A stiff, 0.089 mm diameter PTFE-coated steel wire mandrel was introduced into the distal guide wire lumen of the balloon catheter. One end of the 120 mm ePTFE tube was longitudinally slit across the diameter for a length of 10 mm creating two, 10 mm long, half-tubular flaps. Grasping the flaps, the tube was pulled over the balloon in a proximal direction, i.e., toward the catheter hub. The proximal edges of the flaps were positioned 20 mm past the proximal balloon seal, thus creating a cover over the balloon.

A 10 mm width of the previously described second type of ePTFE film was wrapped transversely over the last 5 mm of the proximal end of the cover, and the 5 mm of bare balloon catheter shaft proximal to the end of the cover, thereby securing the cover to the catheter shaft. Loctite 7701 primer and then Loctite 4981 adhesive (Loctite Corporation, Dusseldorf, GmbH) were applied to the wrapped film and allowed to dry, adhering the cover to the catheter shaft.

The distal end of the cover was longitudinally slit across the diameter for a length of 10 mm such that two equal-width, half tubular flaps were created. The flaps were pulled 180° apart to propagate the slit to the distal end of the balloon shoulder, creating two deployment tabs. The distal tip of the balloon catheter and the overlying part of the cover adjacent to the balloon distal shoulder were primed with Loctite 7701. A small drop of Loctite 4981 adhesive was placed on one side of the catheter approximately 1 mm from the catheter tip, and the corresponding deployment tab was pressed against the catheter for 15 seconds, thereby bonding it to the catheter. This step was repeated on the opposite side of the catheter to adhere the other deployment tab to the catheter.

The packaging sleeve was advanced distally and positioned proximal to the proximal end of balloon to serve as a retraction sheath. The deployment tabs were everted proximally over the cover and adhered to the retraction sheath such that the end of one tab was 10 mm proximal to the end of the other tab using Loctite 7701 primer and Loctite 4981 adhesive. This created 10 mm of slack in the more distally-attached deployment tab.

The balloon was inflated to the nominal inflation pressure (NIP) of 6 atm (~85 psi), and the balloon cover remained intact on the surface of the balloon. The retraction sheath was displaced proximally along the catheter shaft creating tension first on the more proximally-attached deployment tab. Further proximal displacement of the retraction sheath resulted in peeling of one side of the balloon cover from the distal portion of the balloon. Continued proximal displacement of the retraction sheath created tension on the second, more distally-attached deployment tab, followed by peeling of the other side of the balloon cover. Further displacement of the packaging sheath resulted in a continued splitting and peeling back of both tabs in a staggered fashion until the entire balloon was uncovered.

EXAMPLE 2

This example describes construction of a splitting, retractable balloon cover, applied to a medical balloon, wherein the cover material has been treated to render it hydrophilic, all in accordance with the present invention.

A splitting, retractable balloon cover was assembled in accordance with Example 1 and treated with a hydrophilic coating using the following method. Prior to being disposed over the balloon, the balloon cover was fully submerged in a bath of 100% IPA for 30 seconds, then transferred to a bath containing 2% polyvinyl alcohol (g/mL) in deionized (DI) water and allowed to dwell for 20 minutes. The balloon cover was then rinsed in DI water for 15 minutes. Upon rinse completion, the balloon cover was transferred to a bath containing 2% glutaraldehyde (mL/mL) and 1% hydrochloric acid (mL/mL) in DI water. The balloon cover remained in this bath for 15 minutes and was then transferred to a DI water rinse for an additional 15 minutes. The balloon cover was allowed to dry in ambient air for approximately 2 hours and subsequently disposed over the balloon as described in Example 1.

EXAMPLE 3

In this example, effectiveness of the balloon cover in protecting a drug coating was evaluated by subjecting balloons covered in accordance with the present invention and non-covered control balloons to simulated handling and deployment conditions.

Nine 5 mm diameter by 40 mm long PTA balloon catheters were obtained (BMT-035 08QL-504A, Bavaria Medizin Technologie, GmbH). All of the balloons were coated with paclitaxel (Paclitaxel/S, Code N.: 3064055, Indena USA Inc., Seattle, Wash.) and urea (Urea U4884, Sigma-Aldrich Co. LLC, St. Louis, Mo.). The paclitaxel and urea were mixed in a dry ratio of 7:1 by weight, and solubilized in methanol (CHROMASOLV®, for HPLC, ≥99.9%, Sigma-Aldrich Co, LLC, St. Louis Mo.) to achieve a mixture having about 3% solids. Each balloon catheter was positioned over a 0.089 mm mandrel which was then clamped in a vise to allow axial rotation of the catheter. The balloon was then inflated to approximately 30 psi and the catheter rotated about its axis at 60 revolutions per minute (RPM), while 100 µl of the paclitaxel/urea solution was dispensed onto the balloon surface using a 100 µl pipette transited along the length of the rotating balloon. The mass of the applied paclitaxel was calculated from the percent solids in the formulation and the volume dispensed. This resulted in a mass of approximately 2.004 mg of paclitaxel deposited on each balloon.

Three of the balloons were covered with splitting, retractable balloon covers made as described in Example 1. Three of the balloons were covered with splitting, retractable, hydrophilic balloon covers made as described in Example 2. Three of the balloons were left uncovered to serve as controls.

To simulate conditions potentially leading to loss of drug coating during dry handling prior to use, the six covered balloons and three uncovered balloons were each manually tapped against the wall of a clean, dry, 15 ml centrifuge tube for 30 seconds. The balloons were then removed and the contents of the centrifuge tubes were extracted and analyzed via ultra performance liquid chromatography with UV detection (UPLC-UV) for total paclitaxel content.

To simulate conditions leading to drug loss from the balloon during tracking to a treatment site, each of the balloons was then submerged in a clean 15 ml centrifuge tube containing DI water for 30 seconds. The quantity of paclitaxel in the solution was measured by UPLC-UV.

Figure 7:
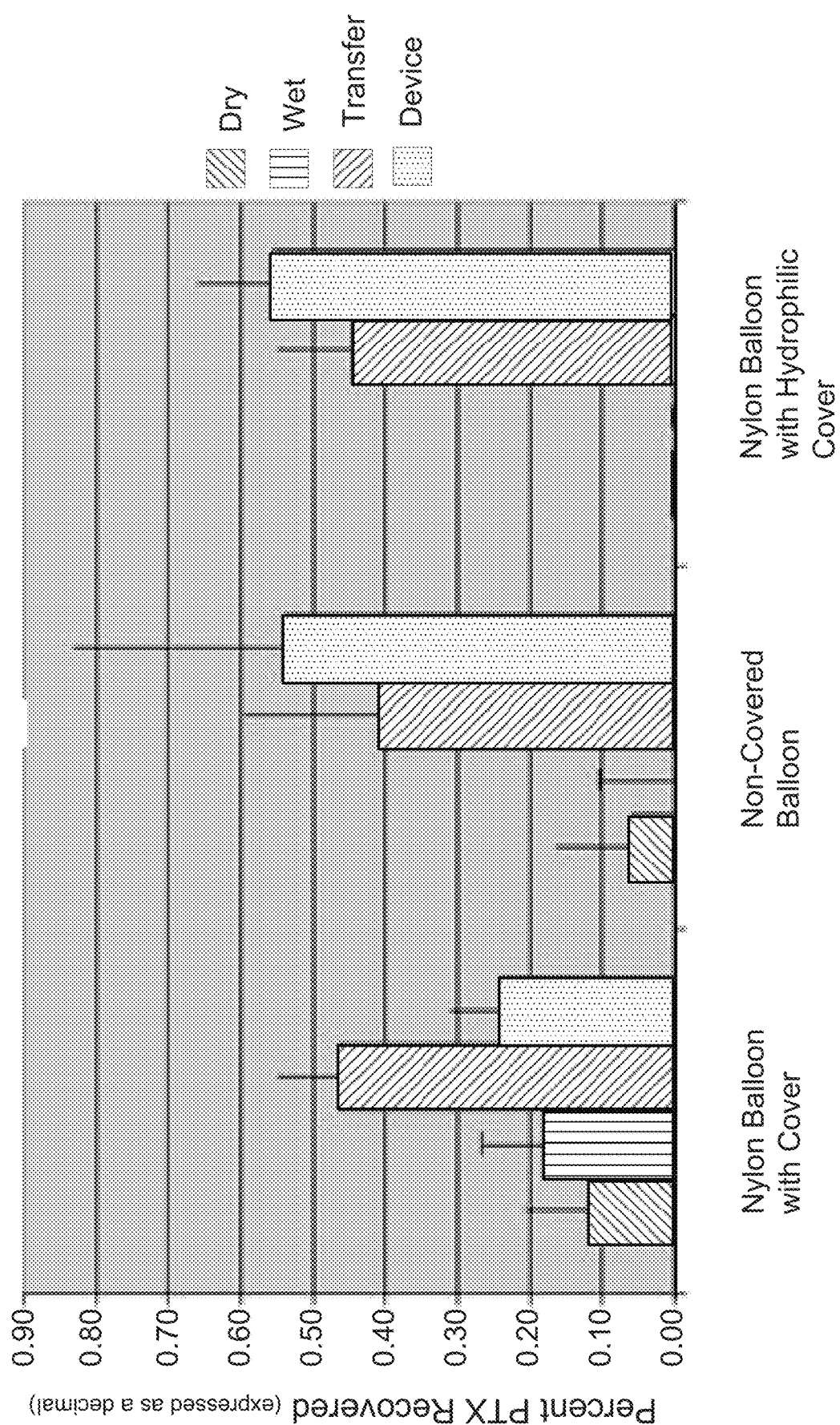
FIG. 7 illustrates a graphical representation of the loss of a therapeutic agent during dry and wet simulated handling for various medical device delivery systems in accordance with the present disclosure.

In both the dry and wet simulated handling tests, devices incorporating the splitting, retractable balloon cover of the present invention demonstrated improved retention of drug coating on the balloons as compared to the non-covered control balloons. The proportion of paclitaxel recovered during the wet and dry simulated handling tests, measured in terms of the percentage of the original quantity coated onto each balloon, is graphically depicted in FIG. 7 and tabulated in Table 1.

TABLE 1

| Device | Dry (%) | StDev | Wet (%) | StDev |
|---|---|---|---|---|
| Non-covered balloon controls | 11.75 | 8.63 | 18.00 | 15.98 |
| Covered balloon | 5.93 | 10.27 | 0.00 | 0.05 |
| Covered balloon - Hydrophilic | 0.00 | 0.00 | 0.00 | 0.00 |

While particular embodiments of the present invention have been illustrated and described herein, the present invention should not be limited to such illustrations and descriptions. It should be apparent that changes and modifications may be incorporated and embodied as part of the present invention within the scope of the following claims.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A medical device comprising:
   an expandable medical device; and
   a tubular sheath surrounding at least a portion of the expandable medical device,
   wherein the tubular sheath is configured to split upon a proximally directed application of tension being applied to a distal end of the tubular sheath, and
   wherein the tubular sheath is configured such that a split portion of the tubular sheath is adapted to be everted inwardly and removed from surrounding the expandable medical device by extending between the tubular sheath and the expandable medical device.

2. The medical device of claim 1, further comprising an activation line coupled to the distal end of the tubular sheath, the activation line extending between the tubular sheath and the expandable medical device.

3. The medical device of claim 2, wherein the sheath is configured to split into a first sheath segment and a second sheath segment, and wherein the activation line includes a first portion attached to the first sheath segment and a second portion attached to the second sheath segment, the first and second sheath segments being adapted to be everted inwardly and removed from surrounding the expandable medical device by extending between the tubular sheath and the expandable medical device.

4. The medical device of claim 1, wherein the tubular sheath has an inner surface and the expandable medical device has an outer surface, and wherein the split portion of the tubular sheath is adapted to be everted inwardly and removed from surrounding the expandable medical device by extending between the inner surface of the tubular sheath and the outer surface of the expandable medical device.

5. The medical device of claim 3, wherein the first sheath segment is removable from surrounding the expandable medical device prior to the second sheath segment being removed from surrounding the expandable medical device.

6. The medical device of claim 3, wherein a length of the first portion of the activation line is shorter than a length of the second portion of the activation line.

7. The medical device of claim 2, wherein the expandable medical device is a first balloon, the medical device further comprising a second balloon having a higher compliance than a compliance of the first balloon, the second balloon being in fluid communication with the first balloon, wherein upon inflation of the second balloon, tension is applied to the activation line.

8. A medical device comprising:
an expandable medical device; and
a tubular sheath surrounding at least a portion of the expandable medical device, the tubular sheath comprising a first sheath layer and a second sheath layer,
wherein the tubular sheath is configured to split upon a proximally directed application of tension being applied to a distal end of the tubular sheath, and
wherein the tubular sheath is configured such that a split portion of the tubular sheath is adapted to be everted inwardly and removed from surrounding the expandable medical device by extending between the first and second sheath layers.

9. The medical device of claim 8, further comprising an activation line coupled to the distal end of the tubular sheath, the activation line extending between the first and second sheath layers.

10. The medical device of claim 9, wherein the sheath is configured to split into a first sheath segment and a second sheath segment, and wherein the activation line includes a first portion attached to the first sheath segment and a second portion attached to the second sheath segment, the first and second sheath segments being adapted to be everted inwardly and removed from surrounding the expandable medical device by extending between the first and second sheath layers.

11. The medical device of claim 10, wherein the first sheath segment is removable from surrounding the expandable medical device prior to the second sheath segment being removed from surrounding the expandable medical device.

12. The medical device of claim 10, wherein a length of the first portion of the activation line is shorter than a length of the second portion of the activation line.

13. The medical device of claim 8, wherein the expandable medical device is one of a balloon and a stent.

14. The medical device of claim 9, wherein the expandable medical device is a first balloon, the medical device further comprising a second balloon having a higher compliance than a compliance of the first balloon, the second balloon being in fluid communication with the first balloon, wherein upon inflation of the second balloon, tension is applied to the activation line.

15. The medical device of claim 8, wherein the tubular sheath comprises an extruded polymeric tube.

16. The medical device of claim 8, wherein the tubular sheath comprises a wrapped polymeric material.

17. The medical device of claim 8, wherein the tubular sheath comprises a distensible and highly oriented polymeric material.

18. The medical device of claim 8, wherein the tubular sheath comprises ePTFE.

19. The medical device of claim 9, wherein a proximal end of the tubular sheath is secured to an elongate member.

* * * * *